(12) United States Patent
Barak (10) Patent No.: US 8,734,826 B2
(45) Date of Patent: May 27, 2014

(54) DEVICE AND METHOD FOR TREATING THE ANAL SPHINCTER

(71) Applicant: Nir Barak, Tel-Aviv (IL)

(72) Inventor: Nir Barak, Tel-Aviv (IL)

(73) Assignee: RDD Pharma, Ltd., Tel Aviv (IL)

( * ) Notice: Subject to any disclaimer, the term of this patent is extended or adjusted under 35 U.S.C. 154(b) by 0 days.

(21) Appl. No.: 14/084,106

(22) Filed: Nov. 19, 2013

(65) Prior Publication Data

US 2014/0074066 A1   Mar. 13, 2014

Related U.S. Application Data

(63) Continuation of application No. 12/087,246, filed as application No. PCT/IL2006/001446 on Dec. 14, 2006, now abandoned.

(60) Provisional application No. 60/754,612, filed on Dec. 30, 2005.

(51) Int. Cl.
  *A61F 13/00*   (2006.01)
  *A61F 6/06*   (2006.01)
  *A01N 61/00*   (2006.01)

(52) U.S. Cl.
  USPC ........... 424/422; 424/430; 424/434; 424/436; 514/1

(58) Field of Classification Search
  None
  See application file for complete search history.

(56) References Cited

U.S. PATENT DOCUMENTS 4,135,514 A * 1/1979 Zaffaroni et al. ............. 424/428
6,331,313 B1 * 12/2001 Wong et al. ................... 424/427
6,685,697 B1 * 2/2004 Arenberg et al. .......... 604/890.1

FOREIGN PATENT DOCUMENTS

GB   2 178 659   *   2/1987

* cited by examiner

*Primary Examiner* — Scott Long
*Assistant Examiner* — Lyndsey Beckhardt
(74) *Attorney, Agent, or Firm* — Greenberg, Traurig, LLP (57) ABSTRACT

A rectally insertable device for localized drug delivery to the anal sphincter of a subject, a method of using the device and the use of the device is disclosed. The device comprises a shell for containing an active pharmaceutical ingredient, the shell being substantially impermeable to the active pharmaceutical ingredient wherein a lower portion of the shell is configured to release the active pharmaceutical ingredient from the shell and wherein when the device is inserted into the rectum of the subject, the lower portion of the shell is proximal to the anal sphincter, such that the active pharmaceutical ingredient is released proximal to the anal sphincter.

16 Claims, 5 Drawing Sheets

DEVICE AND METHOD FOR TREATING THE ANAL SPHINCTER

RELATED APPLICATIONS

This application is a Continuation patent application of U.S. patent application Ser. No. 12/087,246 filed on Jun. 27, 2008, which is a National Phase of PCT Patent Application No. PCT/IL2006/001446 having International filing date of Dec. 14, 2006, which claims the benefit of U.S. Provisional Patent Application No. 60/754,612 filed on Dec. 30, 2005. The contents of the above Applications are all incorporated herein by reference.

FIELD AND BACKGROUND OF THE INVENTION

The present invention relates to devices and methods for the treatment of anorectal disorders, and more particularly to devices and methods for localized delivery of an active pharmaceutical ingredient to the anal sphincter.

Sphincters are circular groups of smooth muscle that control the orifices of hollow organs. Sphincters present throughout the gastrointestinal (GI) tract control the passage of materials through this system of the body. When constricted, the sphincters close orifices leading to the hollow organs, such as the stomach, intestine and anus. In order for the sphincter to open, the muscles must relax.

The rectum is the terminal portion of the large intestine, ending at the anal canal. The anal canal begins where the terminal portion of the large intestine passes through the pelvic floor muscles, and ends at the anal verge. The sphincter that closes the anus (sphincter ani) consists of two sphincter muscle groups. The internal anal sphincter (IAS) is a ring of smooth muscle which surrounds the lower extremity of the rectum and is formed by an aggregation of the involuntary smooth muscle fibers. The internal anal sphincter is under a state of chronic contraction, due both to intrinsic myogenic properties and external innervation. Projections from nerves within the enteric nervous system serve to control the internal anal sphincter. The external anal sphincter (EAS) is a thin flat plane of striated muscle fibers, under voluntary control, adherent to the integument surrounding the margin of the anus.

The anal sphincter keeps the anus closed as stool collects in the rectum. Eventually the pressure on the rectum wall causes the anal sphincter to relax, allowing stool to pass out of the body through the anus. Both the internal and external sphincter muscles need to relax in order to pass stool.

Anorectal disorders include anal sphincter spasm, anal fissures, abscesses, fistulae, ulcers, irritation and itching (pruritus ani), hemorrhoids, incontinence, constipation, inflammation, infection, and cancer.

Anal sphincter spasm is a condition in which the muscles of the internal anal sphincter are under abnormal tension. This may be caused, for example, by local inflammation. The strong contractions of the internal anal sphincter associated with sphincter spasm often give rise to mucosal ischaemia, resulting in anal fissures, which are painful linear ulcers or crack-like tears in the distal anal canal, which, in the short-term, usually involves only the epithelium and, in the long-term, involves the full thickness of the anal mucosa. Anal sphincter spasm can cause sharp pain, especially when opening the bowels. Anal sphincter spasm is also a cause of the pain following rectal surgery or thrombosed hemorrhoids.

Anal fissures may be also be caused by trauma from the passage of a particularly hard or painful bowel movement particularly as a result of constipation. Because of the pain of a fissure, the internal anal sphincter may go into spasm, raising pressure within the anus. This excess pressure makes it harder to pass stool, exacerbating the constipation, increasing the pressure to form a vicious circle. The spasm of the internal anal sphincter can also restrict the blood supply to the anal skin, reducing its ability to heal.

An acute anal fissure is of short duration (less than a month), and usually heals spontaneously or as a result of simple treatments such as a high fiber diet with adequate water intake or the use of bulk laxatives. Warm sitz baths may provide added symptomatic relief (Jensen, 1986). Applications of heat, cold, witch hazel, topical local anesthetics (e.g., lidocaine), topical steroids (e.g., hydrocortisone), stool softeners, and bed rest have also been prescribed to treat rectal pain.

Acute anal fissures which do not heal become chronic anal fissures or anal ulcers. Current treatments of chronic anal fissures are directed at relieving sphincter spasm and include dilatation (under anesthesia), or cutting a part of the sphincter (lateral internal sphincterotomy) to reduce the hypertonicity of the internal anal sphincter muscle. The Standards Task Force of the American Society of Colon and Rectal Surgeons recommends management of chronic anal fissures by "subcutaneous or open lateral internal sphincterotomy, posterior internal sphincterotomy with advanced flap, or manual dilatation". Healing occurs following sphincterotomy in 95% of cases. Successful sphincterotomy (or manual dilatation) is associated with a significant decrease in intra-anal pressure. However, a number of patients experience incontinence following the surgical procedure. These and other complications have driven the search for alternative methods of reducing anal pressure. Research has been directed towards finding a means of non-surgically reducing anal pressure whilst leaving the ring of internal anal sphincter muscle intact.

Pharmacological treatments for reducing anal pressure includes administration of nitric oxide donors, botulinum toxin, muscarinic agents, sympathetic neuromodulators, and calcium channel antagonists as active pharmaceutical ingredients (APIs).

The discovery that nitric oxide is the principal non-adrenergic non-cholinergic inhibitory transmitter mediating relaxation in the internal anal sphincter led to research into exogenous organic nitrates as a source of nitric oxide, to pharmacologically manipulate the internal anal sphincter. Exogenous nitrates are degraded by cellular metabolism, releasing nitric oxide, and in vitro studies have demonstrated that topical application of ointments or pastes containing nitric oxide donors, such as nitroglycerin, glyceryl trinitrate, or isorbide dinitrate, cause a relaxation of internal anal sphincter smooth muscle (Guillemot, 1993; Lacier, 1994; Gorfine, 1995; Schouten, 1996; Carapeti, 1999), resulting in pain reduction and increased fissure healing. More recent studies have suggested that the application of the nitric oxide precursor, L-arginine, causes a reduction in resting anal pressure.

Botulinum toxin is a powerful biological toxin which binds to pre-synaptic cholinergic nerve terminals. The toxin is taken up and acts rapidly to inhibit the calcium-dependent exocytosis of acetylcholine, causing paralysis within a few hours. Neuromuscular transmission resumes after the growth of new axon terminals but clinical weakening of the muscle lasts for 3 to 4 months. Patients treated with botulinum toxin injection into the external anal sphincter showed a reduction in voluntary squeeze pressure and healing of the fissure. However, peri-anal thrombosis has been reported in some patients (Jost, 1997). Injection of botulinum toxin into the internal anal sphincter of patients with anal fissure reduced pain and promoted fissure healing (Gui, 1994).

Muscarinic agents, such as bethanecol, used as a topical cream have been found to reducing resting anal pressure and increased healing of anal fissures (Carapeti, 2000).

Use of sympathetic neuromodulators to reduce internal anal sphincter tone has also been attempted. For example, β-receptor agonist, salbutamol, administered by inhalation, and the $\alpha_1$-antagonist, indoramin, administered orally, have both been shown to reduce resting anal pressure in healthy controls and patients with fissures. However, the reduction has been found to be relatively low, and does not consistently lead to increased fissure healing.

Calcium is known to be important for both agonist-induced contraction of the internal anal sphincter and myogenic tone. Calcium channel antagonists, such as diltiazem have therefore been used in an attempt to modulate resting anal pressure (Jonard and Essamri). Oral diltiazem caused a reduction in resting anal pressure, but was associated with postural hypotension in a number of patients. Topical diltiazem has been shown to reduce resting anal pressure in healthy volunteers, and results in fissure healing. The topical preparation caused a greater reduction in resting anal pressure and healed more fissures with fewer side-effects (Griffin, 2002). The calcium channel blocker, nifedipine, administered as a gel, has also been shown to be effective in reduction of resting anal pressure, resulting in a decrease of anal pain associated with hypertension (Bhardwaj, 2000).

Anorectal abscesses are localized pocket of pus caused by bacterial infection. Abscesses are classified based on their anatomical location. The most commonly described locations are perianal, ischiorectal, intersphincteric, and supralevator. Perianal abscesses are located beneath the skin of the anal canal and do not transverse the external sphincter; ischiorectal abscesses form when suppuration transverses the external sphincter into the ischiorectal space; intersphincteric abscesses result from suppuration contained between the internal and external anal sphincters; and supralevator abscesses result either from suppuration extending cranially through the longitudinal muscle of the rectum from an origin in the intersphincteric space to reach above the levators, or as a result of primary disease in the pelvis (e.g., appendicitis, diverticular disease, gynecological sepsis). Certain conditions, such as Crohn's disease can increase the risk of abscess in and around the anal canal. Patients with conditions that reduce the body's immunity, such as cancer or AIDS, are also more likely to develop anal abscesses. An abscess causes tenderness, swelling, and pain. The patient may also complain of fever, chills, and general weakness or fatigue. Abscesses may be treated by drainage, or by administration of antibiotics, such as ampicillin, cefazolin, and clindamycin. Analgesics, such as meperidine, may also be prescribed.

Anal fistulae are tiny channels or tracts that develop in the presence of inflammation and infection. These may or may not be associated with an abscess, but like abscesses, certain illnesses such as Crohn's disease can cause fistulae to develop. The channel usually runs from the rectum to an opening in the skin around the anus. Treatment for fistulae varies depending on the cause and extent of the fistula, but often involves surgical intervention combined with antibiotic therapy.

Itchy skin around the anus (pruritus ani) can have many causes, including skin disorders (such as psoriasis and atopic dermatitis), diseases such as diabetes or liver disease, anal disorders (such as skin tags or draining fistulas), cancers such as Bowen's disease, allergic reactions (such as contact dermatitis caused by anesthetic preparations applied to the skin, various ointments, or chemicals used in soap), lack of hygiene or infections with fungi, bacteria, or parasites. Itching may also be a side effect of antibiotics, especially tetracycline. Treatment may comprise administration of corticosteroid creams, antifungal creams or simply washing.

The term hemorrhoids refers to a condition in which the veins around the anus or lower rectum are swollen and inflamed. Hemorrhoids may result from straining to move stool. Other contributing factors include pregnancy, aging, chronic constipation or diarrhea, and anal intercourse. Hemorrhoids occur both inside and above the anus (internal) or under the skin around the anus (external). APIs for the treatment of hemorrhoids include nitrates, such as isosorbide dinitrate (Briel, 2000), or calcium channel blockers.

Natural treatments for hemorrhoids include the use of herbs and dietary supplements that strengthen vein walls as APIs, such as butcher's broom, horse chestnut, bromelains, bioflavanoids, and Japanese pagoda tree extracts; or natural astringents and soothing agents such as witch hazel, cranesbill and aloe vera (MacKay, 2001).

Constipation and incontinence may both be caused by a combination of interrelated factors which include the sphincter muscles, rectal and anal sensation, as well as stool composition. Incontinence is associated with a reduction in anal pressure, which results principally from the activity of the anal sphincter muscles. Incontinence may be treated by APIs which enhance anal tone, such as inhibitors of nitric oxide synthase, or phenylephrine (Cook, 2001). Constipation may be treated with laxatives, such as bulk laxative, osmotic laxatives, stimulant laxatives, poorly absorbed sugars, stool softeners, enemas, cholinergic agents or prokinetic agents.

Certain APIs for the treatment of anorectal disorders, such as antibiotics, may be administered systemically, for example orally or by injection. This method is associated with a high occurrence rate of systemic side effects that limit its use, and by the potential for drug interactions with other medications prescribed to the patient. The oral route may be inefficient, with poor bioavailability of high dose or low solubility APIs, such that only part of the dose is absorbed. Due to the "first-pass" effect, APIs absorbed orally are transported to the general circulation via the liver. Thus APIs which are extensively metabolized will be metabolized in the liver during absorption. Furthermore, food and gastrointestinal motility can effect API absorption. Absorption is slower with food for tetracyclines and penicillins. Orally administered antibiotics may kill normal gut flora and allow overgrowth of fungal varieties. Thus, an antifungal agent may be required in addition to the antibiotic.

Administration by rectal injection is limited by its high cost, since these performed only by medically qualified personnel, and is reserved for APIs with long activity time (such as botulinum).

Another method of API application is by the use of suppositories. Suppositories are solid, bullet-shaped preparations designed for easy insertion into the anus. The API is incorporated into a base, which melts at body temperature and gradually spreads over the lining of the rectum.

U.S. Pat. No. 5,413,793 teaches a multiphase pharmaceutical composition for combating an anorectal disease, in which a first phase contains an active ingredient and a second phase provides a layer of silicone oil to cover the treatment area, to repel water therefrom, so protecting the area from erosion by aqueous media. This composition is in the form of a suppository, which may be provided in any standard suppository base.

Upon administration of an active pharmaceutical ingredient using a suppository, the API diffuses out of the suppository in an uncontrolled manner into the rectum. Since the rectum has a rich blood supply, the API is absorbed rapidly into the blood leading to systemic delivery of the API rather than topical delivery. For topical administration, administration via suppository is associated with a high rate of adverse effects, possible interactions with other APIs as well as variation in the bioavailability of certain APIs, in particular those which undergo extensive first-pass elimination.

For treatment of the anal sphincter, topical administration of a topical preparation directly to the rectal area is preferred. Currently known preparations are provided in the form of a powder, spray, ointment, paste, cream, lotion, gels, or solution. For example, U.S. Pat. No. 6,395,736 teaches compositions and methods for the treatment of anorectal disorders in which combinations of nitric oxide donors, phosphodiesterase inhibitors, superoxide scavengers, β-adrenergic agonists, cyclic adenosine monophosphate-dependent protein kinase activators, $\alpha_1$-adrenergic antagonists, L-type calcium channel blockers, estrogens, adenosine triphosphate-sensitive calcium channel activators and smooth muscle relaxants are used. These are administered by any of the standard dosage forms listed above.

The prior art dosage forms for direct topical application for the treatment of anorectal disorders, such as powders, sprays, ointments, pastes, creams, lotions, gels, and solutions are messy and inconvenient to use. Application of the composition several times daily is required, which is inconvenient and disruptive to daily activities, and may reduce patient compliance. Another problem associated with direct topical application is the possible soiling of clothes, that might affect social activity.

The prior art does not teach or suggest methods or devices for convenient, highly localized delivery of APIs to the anal sphincter.

SUMMARY OF THE INVENTION

The present invention successfully addresses the shortcomings of the known methods of treating anorectal disorders by providing novel devices and methods for delivery of an active pharmaceutical ingredient (APIs) to the anal sphincter.

According to one aspect of the present invention there is provided a rectally insertable drug delivery device for localized delivery of an API, to the anal sphincter of a subject, comprising a shell for containing an API, which is substantially impermeable to the API and has a lower portion configured to release the API from the shell, such that when the device is inserted into the rectum of the subject, the lower portion of the shell is proximal to the anal sphincter, such that the API is released proximal to the anal sphincter.

According to another aspect of the present invention, there is provided a method of delivering a API to the anal sphincter of a subject, the method comprising providing a rectally insertable drug delivery device comprising a shell for containing an API, the shell being substantially impermeable to the API, and having a lower portion configured to release the API from the shell; and inserting the device into the rectum of the subject, wherein the lower portion of the shell is proximal to the anal sphincter, such that the API is released proximal to the anal sphincter.

According to further features in preferred embodiments of the invention described below, the API optionally forms a part of a pharmaceutical composition, further comprising a pharmaceutically acceptable carrier. The carrier may optionally be a liquid or semi-solid (such as a paste, gel, ointment, or foam at room temperature).

Alternatively, the carrier may optionally have a melting point in the range of from about 23° C. to about 37.5° C., such that the carrier becomes a liquid upon insertion of the device into the rectum. According to still further features in this embodiment, the carrier may be, for example, coconut oil, cocoa butter, polyethylene glycol, glycerinated gelatin, a hydrogenated vegetable oil, a fatty acid esters of a polyethylene glycols, a glycolsurfactant polyethylene glycol, and a polyoxyethylene derivatives of sorbitan monostearate or polyoxyl-40 stearate, or a mixture thereof.

According to further features in any of the described preferred embodiments, the lower portion of the shell optionally comprises an aperture positioned proximal to the anal sphincter. Alternatively, the lower portion of the shell may optionally comprise a membrane impermeable to the API and permeable to water.

According to further features in the described embodiments in which the carrier is a liquid or liquefies upon insertion, the lower portion of the shell may optionally comprise a wick, having an upper end in contact with the carrier and a lower end which protrudes from the lower portion of the shell, such that the wick is proximal to the rectal sphincter when the device is inserted into the rectum.

According to a feature of the present invention, when the carrier is a liquid or liquefies upon insertion, the lower portion of the shell may optionally comprise a to sponge (or substantially similar component), having an upper end in contact with the carrier and a lower end which protrudes from the lower portion of the shell.

According to still further features in the described preferred embodiments, the lower portion of the shell may further comprise a removable closure.

According to still further features in the described preferred embodiments, a release-controlling system may be provided within the shell for controlling delivery of the API to the lower portion of the shell.

The release-controlling system may comprise, for example, a reservoir compartment having an outlet which controls delivery of the API to the lower portion of the shell.

Alternatively, the release-controlling system may comprise a controlled-release formulation comprising at least one release-controlling excipient, such as, for example, a linear polymer, a burst-controlling agent or a sustained-release matrix, such as sodium alginate.

According to still further features in the described preferred embodiments, an outer surface of the shell may be provided with a lubricant layer, which may optionally comprise a local anesthetic.

According to still further features in the described preferred embodiments, the shell may optionally be provided with a rounded tip.

According to still further features in the described preferred embodiments, the shell may optionally be collapsible upon release of the API.

According to further features in any of the described preferred embodiments, the method or device may be used in the treatment of a condition associated with a disorder of the anal sphincter, such as, for example, anal sphincter spasm, anal fissure, anal abscess, anal fistula, anal ulcer, pruritus ani, hemorrhoids, incontinence, constipation, inflammation, infection, cancer, or combinations thereof.

According to further features in any of the described preferred embodiments, the API for use in the method or device may be any one of a herbal extract, bee pollen, a muscle relaxant, a local anesthetic, an antibiotic, an anti-inflammatory agent, a nitric oxide donor, botulinum toxin, a muscarinic agent, a sympathetic neuromodulator, a calcium channel antagonist, a phosphodiesterase inhibitor, a superoxide scavenger, a cyclic adenosine monophosphate-dependent protein kinase activator, an adenosine triphosphate-sensitive calcium channel activator and mixtures thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

EMBODIMENTS OF THE INVENTION

The present invention is of a device and method for controlled administration of an API directly to the anal sphincter.

The principles and operation of the compositions and methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which the invention belongs. In addition, the descriptions, materials, methods, and examples are illustrative only and not intended to be limiting. Methods and materials similar or equivalent to those described herein can be used in the practice or testing of the present invention.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to mariners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Implementation of the methods of the present invention involves performing or completing selected tasks or steps manually, automatically, or a combination thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the singular form "a," "an," and "the" include plural references unless the context clearly dictates otherwise. For example, the term "a compound" or "at least one compound" may include a plurality of compounds, including mixtures thereof.

Figure 1:
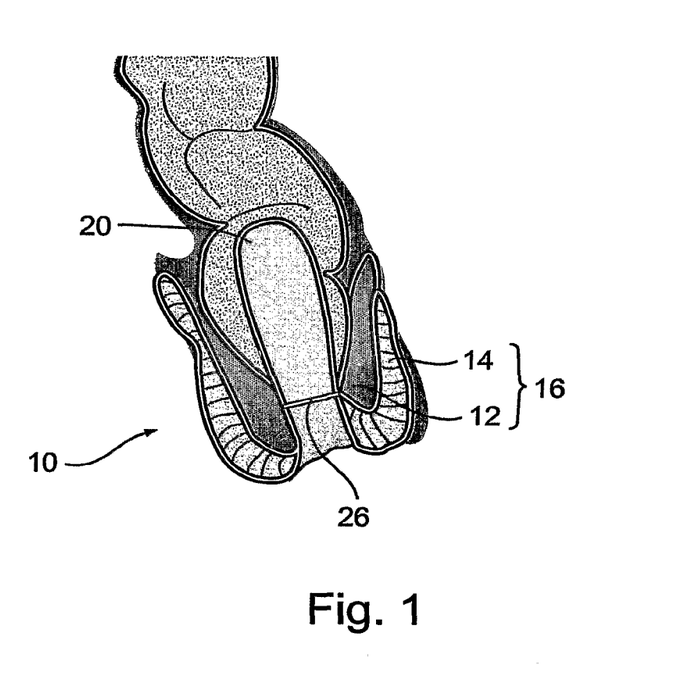
FIG. 1 illustrates the device of the present invention inserted within the rectum.

For purposes of better understanding the present invention, reference is first made to FIG. 1, illustrating the anatomy of the rectum with a device 20 of the present invention inserted therein. The rectum 10 is the lower 10 to 15 cm of the large intestine. The terminal thickening of the inner visceral smooth muscle layer of the rectal wall forms the internal anal sphincter 12, which is surrounded by the external anal sphincter 14, which together comprise the anal sphincter 16. Device 20 is inserted within rectum 10 such that a lower portion 26 of device 20 is proximal to anal sphincter 16.

Figure 2A:
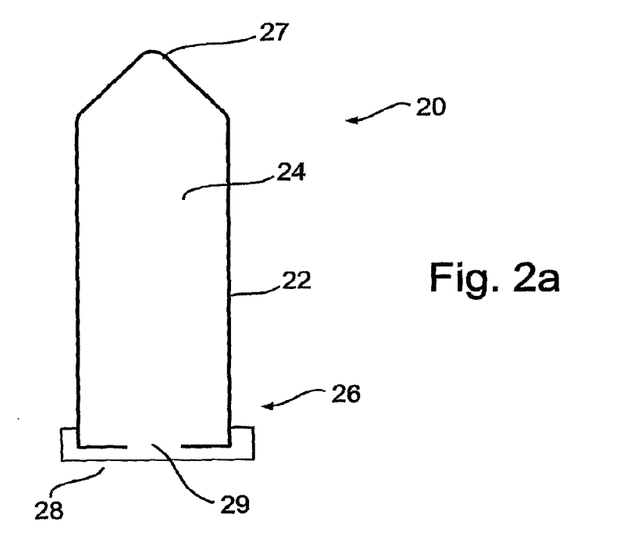
FIGS. 2a-2b schematically illustrate a device for delivery of an API to the rectal sphincter, in accordance with a preferred embodiment of the present invention.
Figure 2B:
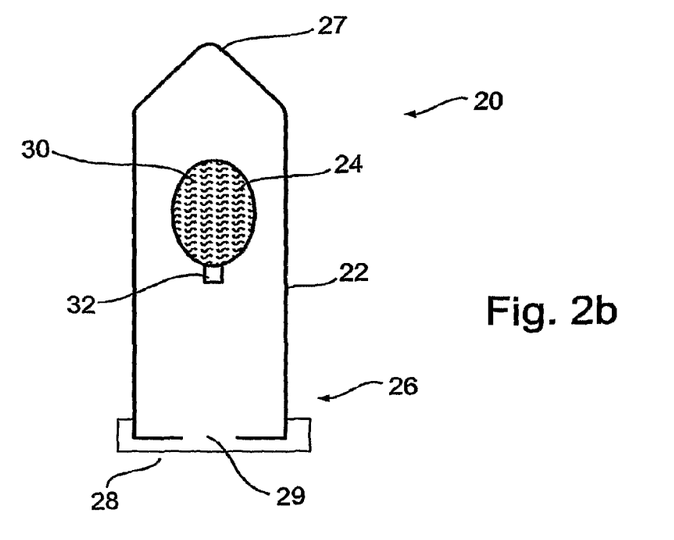

Referring now to FIG. 2, a rectally insertable device 20 in accordance with a preferred embodiment of the present invention is illustrated. Device 20 comprises a shell 22 for containing an active pharmaceutical ingredient (API) 24. The upper end and sides of shell 22 are preferably smoothly continuous, and are formed from a material which is impermeable to API 24, such that API 24 is unable to pass through shell 22 into the rectum. Shell 22 may be constructed from at least one layer of any non-irritating material which is impermeable to API 24 and which is sufficiently strong not to tear during insertion into the rectum. The at least one layer should be thin enough so that shell 22 sufficiently flexible to avoid unnecessary patient discomfort. Shell 22 should also be compatible with, and not degrade substantially in reaction to a lubricant used in conjunction with device 20. Non-limiting examples of materials suitable for use in constructing a shell 22 include rubber, latex, silicon, polyvinylchloride, and polyurethane. Preferably, shell 22 is provided with a rounded tip 27 to minimize discomfort to the subject during insertion.

Shell 22 is provided with a lower portion 26 through which API 24 is released. The dimensions of device 20 are such that when device 20 is inserted into the rectum of a subject, lower portion 26 is positioned proximal to the anal sphincter, thereby releasing API 24 directly in the vicinity of the anal sphincter.

API 24 preferably forms a part of a pharmaceutical composition, further comprising a pharmaceutically acceptable carrier.

In embodiments of the present invention, a carrier is a liquid at room temperature.

In embodiments of the present invention, a carrier is a material having a melting point in the range of from about 23° C. to about 37.5° C., such that the carrier is solid at normal room temperature, but melts due to the body temperature of the subject upon insertion of device 20 into the rectum. Non-limiting examples of suitable carriers include coconut oil, cocoa butter, polyethylene glycol, glycerinated gelatin, hydrogenated vegetable oils, fatty acid esters of polyethylene glycols, glycolsurfactant polyethylene glycols, and nonionic surfactant materials such as polyoxyethylene derivatives of sorbitan monostearate and polyoxyl-40 stearate In embodiments of the present invention, a carrier is a semi-solid carrier, such as for example, a paste, gel, ointment, or foam.

The manner in which API 24 is released from device 20 is at least partly dependent on the form of carrier used. Release of API 24 through lower portion 26 may occur, for example, through an aperture 29 provided in lower portion 26. In embodiments wherein the carrier is a liquid (either at room temperature, or upon melting following insertion of device 20 into the rectum), aperture 29 may optionally be of a size which enables slow, for example drop-wise, release of the carrier through aperture 29. In such embodiments, lower portion 26 is further provided with a removable closure 28, to retain API 24 in shell 22 until required, and to protect the associated pharmaceutical composition from contamination. Optionally, closure 28 is provided in a form which may removed prior to insertion of device 20 in the rectum, such as, for example, a cap, a pierceable membrane, a plug, or the like.

In embodiments wherein the carrier is a semi-solid, aperture 29 is preferably of a dimension greater than that used for release of a liquid carrier, such that upon insertion of device 20 into the rectum of a subject, pressure exerted on shell 22 by contraction of the anal sphincter causes the carrier to be squeezed out through aperture 29.

According to an alternative embodiment of the present invention, lower portion 26 comprises a membrane which is impermeable to API 24, but permeable to water from the rectum. In such an embodiment, API 24 is either capable of developing an osmotic pressure, or an osmotic additive is added to the pharmaceutical composition. When device 20 is inserted into the rectum of a subject, water is imbibed into shell 22 due to the difference in osmotic pressure across the membrane, producing pressure inside shell 22, which eventually causes the membrane to burst. The time delay between the time device 20 is inserted into the rectum and the time at which the membrane bursts can be controlled, for example, by varying the thickness or area or material of composition of the semi-permeable membrane to increase or decrease the rate of permeation of water into the enclosure.

In any of the embodiments of the present invention, shell 22 is optionally configured so as to be collapsible during release of API 24, that is to say as the pharmaceutical composition including API 24 is released from shell 22, shell 22 to inwardly collapses. In such a way, the formation of subpressure that potentially prevents release of API 24 from shell 22 is avoided.

Following release of API 24, device 20 is optionally expelled during a bowel movement. Alternatively, device 20 may be provided with a removal cord which protrudes out of the anus, and which can be used to remove device 20 after use. Also alternatively, the material of shell 22 may be soluble or biodegradable within the rectum.

According to a further feature of an embodiment of device 20, shell 22 is optionally hollow, and the carrier containing API 24 is contained within the hollow interior of shell 20.

According to a further feature of an embodiment of device 20, a release-controlling system 30 is optionally further provided within shell 22 for containing the composition. In embodiments in which the carrier is a liquid, release-controlling system 30, may comprise, for example, a substantially closed reservoir provided with a rate-limiting outlet 32 which controls the rate of delivery of API 24 to lower portion 26 of shell 20. Outlet 32 may comprise for example, a suitably sized aperture, through which API 24 passes at a desired rate, or a membrane which is permeable to API 24.

Alternatively, the release-controlling system may comprise a formulation for providing the API in controlled-release form, such as sustained-release or delayed-release form.

Sustained-release forms release the API over a sustained period of time following insertion of device 20 into the rectum of the patient. Examples of such formulations include those in which API 24 is embedded in a matrix within shell 22 from which it is released by diffusion or erosion; those in which the composition within shell 22 is coated with a release rate-controlling membrane, such as a semi-permeable membrane, allowing the API to diffuse across the membrane or through liquid filled pores within the membrane.

A non-limiting example of a sustained release matrix comprises sodium alginate and a calcium salt. Suitable calcium salts for use in such a matrix include calcium phosphate, dicalcium phosphate, calcium chloride, calcium carbonate, calcium acetate, and calcium gluconate. Other pharmaceutically acceptable calcium salts known in the art may also be used. The amount of calcium salt in the matrix must be sufficient to cross-link with the alginate when exposed to rectal fluids such that a gel matrix is formed from which the API is slowly released. Such a matrix may provide slow release for a period of up to about 24 hours after administration. Alternatively, the matrix may comprise a polymer, such as polyethylene glycol.

Alternatively, sustained-release forms may comprise release-sustaining polymers. Such polymers are preferably high molecular weight linear polymers, and having an affinity for water, which are only slowly biodegradable. Examples of linear polymers which can be used for sustaining release include, without limitation, methylcellulose, hydroxyproplymethylcellulose, hydroxymethylcellulose, polyvinyl alcohols, polyvinyl pyrrolidones, polyacrylamides, polyethylene oxides and certain modified starches.

Pulsatile-release formulations release the active compound after a certain period of time following insertion of the device into the rectum of the patient. The release may then be in the form of immediate- or sustained-release. Examples of such formulations include those in which the composition is present within shell 22 in a capsule containing an erodible plug or compositions comprising a burst controlling agent.

The burst controlling agent preferably comprises a cross-linked, water insoluble polymer for controlling the rate of penetration of water into the core and raising the osmotic pressure inside the core. Such a burst controlling agent is preferably able to swell upon contact with liquid. The water insoluble polymer is optionally selected from the group consisting of a cross-linked polysaccharide (such as insoluble metal salts or cross-linked derivatives of alginate, pectin, xanthan gum, guar gum, tragacanth gum, and locust bean gum, carrageenan, metal salts thereof, and covalently cross-linked derivatives thereof), water insoluble starch, microcrystalline cellulose, water insoluble cross-linked peptide, water insoluble cross-linked protein, water insoluble cross-linked gelatin, water insoluble cross-linked hydrolyzed gelatin, water insoluble cross-linked collagen modified cellulose (such as cross-linked forms of any of hydroxypropylcellulose, hydroxypropylmethylcellulose, hydroxyethylcellulose, methylcellulose, carboxymethylcellulose, and metal salts of carboxymethylcellulose), and cross-linked polyacrylic acid.

The composition may optionally be provided as a dual release formulation, wherein API 24 in immediate release form is combined with a controlled-release dose of either the same API, or of an additional API. For example, a bilayer formulation can be provided within shell 22, with one layer containing immediate release API and the other layer containing the same or a different API embedded in a matrix from which it is released by diffusion or erosion. Alternatively, one or more immediate release beads or pellets can be combined with one or more beads which are coated with a release rate-controlling membrane within shell 22 to give a dual release formulation.

Figure 3:
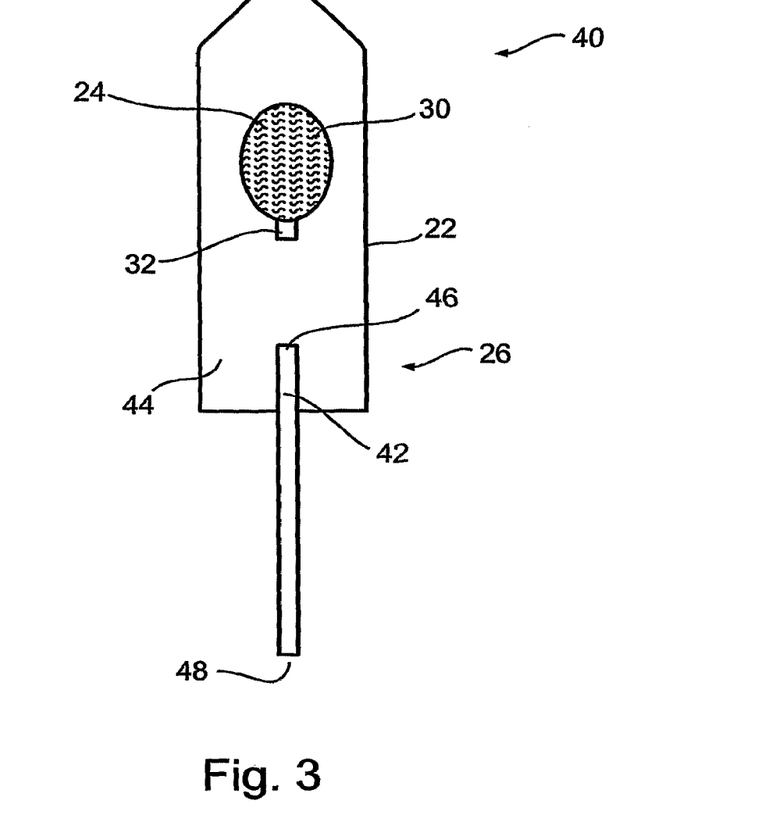
FIG. 3 schematically illustrates a device comprising a wick for the delivery of an API to the rectal sphincter, in accordance with a preferred embodiment of the present invention.

FIG. 3 illustrates an embodiment of the present invention in which a lower portion 26 of device 40 comprises a wick 42, extending through an aperture in substantially closed lower surface 44 of lower portion 26, such that API 24, in a carrier which is either liquid at room temperature, or becomes liquid after insertion into the rectum, is delivered from shell 22 to the proximity of the anal sphincter by capillary action. Wick 42 is configured such that an upper end 46 is in contact with API 24 during delivery of API 24 to the anal sphincter, and a lower end 48 is positioned proximal to the anal sphincter upon insertion of device 20 into the rectum. Upper end 46 of wick 42 may, for example, be positioned in direct contact with the liquid carrier, either within hollow interior of shell 22, or, in embodiments comprising reservoir 30, within the reservoir. Alternatively, where reservoir 30 is provided, wick 42 may optionally be positioned such that API 24 is delivered to upper end 46 of wick 42 through reservoir outlet 32. Wick 42 may be constructed from any suitable material known in the art, such as, for example, woven fabric, unwoven fabric, fiber, gauze, cotton, linen or wool.

Figure 4A:
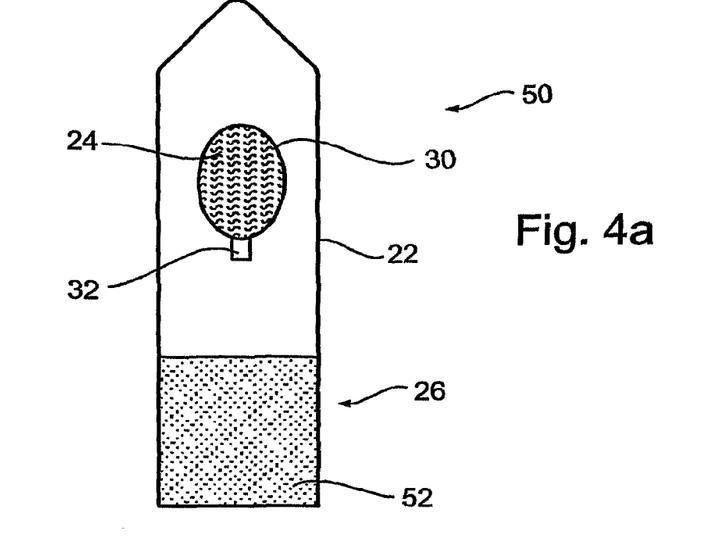
FIGS. 4a-b schematically illustrate a device comprising a sponge for the delivery of an API to the rectal sphincter, in accordance with a preferred embodiment of the present invention.
Figure 4B:
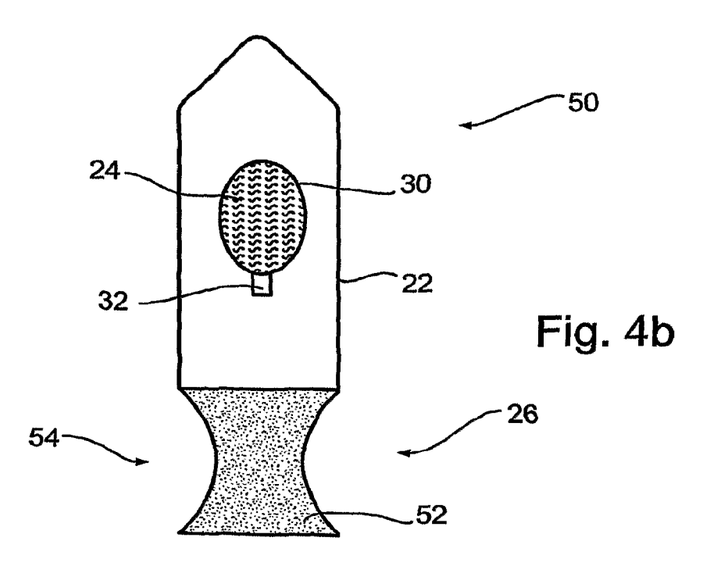

FIG. 4a illustrates a device 50 in which lower portion 26 comprises a sponge 52 or similar material, which is capable of absorbing or adsorbing API 24 (liquid or in a liquid carrier) and swelling. Preferably, API 24 is provided within reservoir 30 and is delivered to sponge 52 at an appropriate rate through reservoir outlet 32. API 24 permeates, and is retained within, sponge 52. Upon insertion of device 20 into the rectum, sponge 52 is squeezed by pressure exerted by the anal sphincter, and API 24 is released from sponge 52 proximate to the point of pressure 54, as shown in FIG. 4b.

Alternatively, in embodiments wherein the carrier is a semi-solid, sponge 52 of device 50 is replaced by an aperture (not shown). The composition is squeezed out through this aperture due to pressure exerted on shell 22 by the contracted anal sphincter following insertion of device 50 into the rectum.

Figure 5:
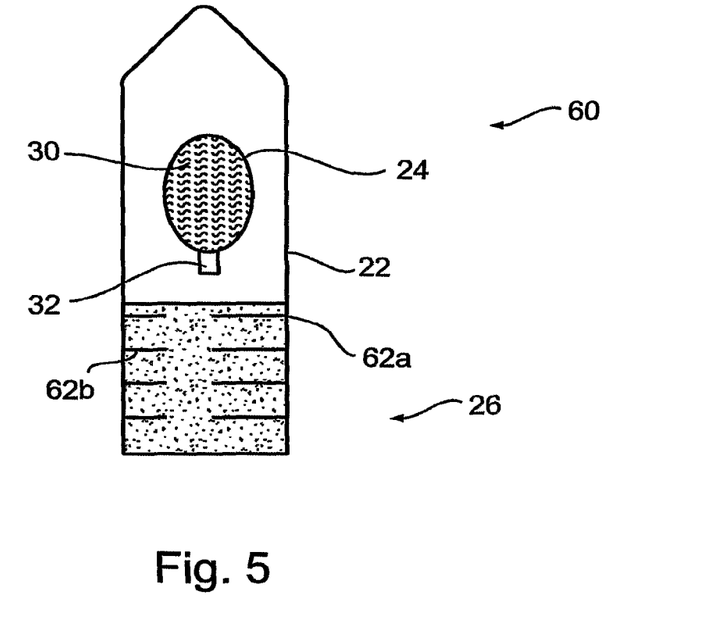
FIG. 5 schematically illustrates a device comprising internal flanges for the delivery of an API to the rectal sphincter, in accordance with a preferred embodiment of the present invention.

FIG. 5 illustrates a further alternative device 60 in which lower portion 26, which is constructed from a material which is permeable to API 24, is provided with a series of opposing internal flanges 62a, 62b, each attached to one side of lower portion 26, and arranged perpendicular to the longitudinal axis of device 60, such that the interior of lower portion 26 is partially obstructed. Flanges 62a, 62b are constructed from a material which is impermeable to API 24. Upon insertion of device 60 into the rectum, pressure exerted by the anal sphincter causes opposing flanges 52a, and 52b to be brought into contact with each other, thereby providing a full closure of the interior of lower portion 26. API 24 is thus released from shell 22 only above the closure.

In any of the embodiments of the present invention including embodiments described herein, an outer surface of shell 22 may be provided with a layer of a lubricant to ease insertion. Further optionally, such a lubricant includes a local anesthetic, such as lidocaine hydrochloride to alleviate pain, particularly in patients with hemorrhoids or inflammatory conditions.

According to a further embodiment of the present invention, there is provided a method of delivering an API to the anal sphincter of a subject, which method comprises inserting a device according to any of the embodiments described above, containing an API, into the rectum of a subject in need thereof, such that the API is released proximal to the anal sphincter.

The device or method of the present invention may be used for the treatment of a condition associated with a disorder of the anal sphincter. Such conditions include, without limitation, anal sphincter spasm, anal fissure, anal abscess, anal fistulae, anal ulcer, pruritus ani, hemorrhoids, incontinence and constipation, cancer, infection, inflammation, or combinations thereof.

In any of the embodiments of the present invention, API 24 is a therapeutically effective amount of any API used for treatment of a disorder of the anal sphincter. Examples of APIs which may be used in accordance with the teachings of the present invention of the present invention include, without limitation, a herbal extract, bee pollen, a muscle relaxant, a local anesthetic, an antibiotic, an anti-inflammatory agent, a nitric oxide donor, botulinum toxin, a muscarinic agent, a sympathetic neuromodulator, a calcium channel antagonist, a phosphodiesterase inhibitor, a superoxide scavenger, a cyclic adenosine monophosphate-dependent protein kinase activator, an adenosine triphosphate-sensitive calcium channel activator and mixtures thereof.

The term "therapeutically effective amount" or "pharmaceutically effective amount" denotes that dose of an APIU or a composition comprising the API that will provide the therapeutic effect for which the API is indicated.

Examples of herbal extracts suitable for use in the device or method of the present invention include, without limitation, aloe vera, American cranesbill (*Geranium maculatum*), balsam of peru (*Myroxylon pereirae*), bilberry (*Vaccinium myrtillus*), bioflavanoids, bistort (*Polygonurn bistorta*), bromelains (*Ananas comosus*), burdock (*Arctium lappa*), butcher's broom (*Ruscus aculeatus*), chamomile (*Anthemis nobilis*), cranesbill (Geraniaceae), horse chesnut (*Aesculus hippocastanium*), indigo (*Baptisia tinctoria*), Japanese pagoda tree (*Sophora japonica*), oak tree (Querceae), periwinkle (*Vinca major, Vinca minor*), St. John's wort (*Hypericum perforatum*), stone root (*Collinsonia canadensis*), vervain (*Verbena officinalis*), witch hazel (*Hamamelis virginiana*), yerba santa (*Eriodictyon glutinosum*) as well as extracts of plants not listed including tannin and gallic acid.

Examples of muscle relaxants suitable for use in the device or method of the present invention include, without limitation, magnesium and salts thereof, cyclobenzaprine, baclofen, ketocam, methocarbamol, and carisoprodol.

Examples of local anesthetics suitable for use in the device or method of the present invention include, without limitation, mepricaine, proparacaine, prilocaine, ropivacaine, benzocaine, bupivacaine, butamben picrate, chlorprocaine, cocaine, dibucaine, dimethisoquin, dyclonine, etidocaine, hexylcaine, ketamine, lidocaine, mepivacaine, pramoxine, procaine, tetracaine, salicylates and derivatives, esters, salts and mixtures thereof.

Examples of anti-inflammatory agents suitable for use in the device or method of the present invention include, without limitation, a non-steroidal anti-inflammatory agent (such as piroxicam, isoxicam, tenoxicam, sudoxicam, CP-14,304, aspirin, disalcid, benorylate, trilisate, safapryn, solprin, diflunisal, fendosal, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, mefenamic, meclofenamic, flufenamic, niflumic, tolfenamic acid, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, phenylbutazone, oxyphenbutazone, feprazone, azapropazone, trimethazone, and mixtures thereof); or a steroidal anti-inflammatory agent (such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof).

Examples of suitable antibiotics include amanfadine hydrochloride, amanfadine sulfate, amikacin, amikacin sulfate, aminoglycosides, amoxicillin, ampicillin, ansamycins, bacitracin, beta-lactams, candicidin, capreomycin, carbenicillin, cephalexin, cephaloridine, cephalothin, cefazolin, cephapirin, cephradine, cephaloglycin, chloramphenicols, chlorhexidine, chlorhexidine gluconate, chlorhexidine hydrochloride, chloroxine, chlorquinaldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erythromycin stearate, farnesol, floxacillin, gentamicin, gentamicin sulfate, gramicidin, griseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenamine, methenamine hippurate, methenamine mandelate, methicillin, metronidazole, miconazole, miconazole hydrochloride, minocycline, minocycline hydrochloride, mupirocin, nafcillin, neomycin, neomycin sulfate, netilmicin, netilmicin sulfate, nitrofurazone, norfloxacin, nystatin, octopirox, oleandomycin, orcephalosporins, oxacillin, oxytetracycline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, yrothricin and derivatives, esters, salts and mixtures thereof.

Non-limiting examples of nitric oxide donors include nitroglycerin, glyceryl trinitrate, isorbide dinitrate, isosorbid mononitrate, L-arginine, amylnitrate, and mixtures thereof.

Examples of suitable sympathetic neuromodulators include, without limitation, β-receptor adrenergic agonists, such as albuterol, bitolterol formoterol, salbutamol, metaproternol, terbutaline, fenterenol, salmefamol, carbuterol, seteronol, quinprenaline, nylidrin and oxyfedrine; and α-adrenergic antagonists, such as indoramin, prazosin, terazosin, doxazosin, and mixtures thereof.

Non-limiting examples of calcium channel antagonists include diltiazem, nifedipine, nicardipine, verapamil, nimodipine, lercanidipine, felodipine, nisolidipine, amlodipine, bepridil, and mixtures thereof.

Examples of suitable phosphodiesterase inhibitors include theophylline, ibudilast, pentoxifylline, papaverine, dipyramidole, amrinone, sildenefil, tadolfil, vardenafil, and milrinone.

Examples of suitable muscarinic agents include bethenecol, oxotremorine, arecoline, pilocarpine, and methacholine and RS-86.

According to any of the embodiments of the present invention described above, the API optionally and preferably forms a part of a pharmaceutical composition. The pharmaceutical composition comprises, in addition to the API, a pharmaceutically acceptable carrier, and may optionally further comprise one or more components selected from binding agents, stabilizers, diluents, excipients, osmotic additives, surfactants, flavors, and odorants. Further optionally, the composition may comprise at least one additional API.

As used herein a "pharmaceutical composition" refers to a preparation of one or more active ingredients, including those explicitly described herein, either compounds or physiologically acceptable salts thereof, with other chemical components such as other APIs, physiologically suitable carriers and excipients.

As used herein, the term "pharmaceutically acceptable" means approved by a regulatory agency, e.g. of the Federal or a state government of the United States or listed in the U.S. Pharmacopeia or listed in another recognized pharmacopeia for use in animals, and more particularly in humans. Herein, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

As used herein, the term "carrier" refers to a diluent, adjuvant, excipient, or vehicle with which the therapeutic is administered.

Herein the term "excipient" refers to an inert substance added to a pharmaceutical composition to further facilitate processes and administration of the active ingredients.

Pharmaceutical compositions used in conjunction with the present invention may be manufactured by processes well known in the art, e.g., by means of conventional mixing, dissolving, or emulsifying processes.

Suitable pharmaceutical carriers in the context of the present invention can be liquids, preferably sterile, such as water and oils, including those of petroleum, animal, vegetable or synthetic origin, such as peanut oil, soybean oil, mineral oil, sesame oil and the like.

Techniques for formulation and administration of active pharmaceutical ingredients may be found in "Remington's Pharmaceutical Sciences," Mack Publishing Co., Easton, Pa., latest edition, which is incorporated herein by reference as if fully set forth herein.

Devices of the present invention may, if desired, be presented in a pack, such as an FDA approved kit, which may contain one or more individual devices containing the active ingredient. The pack may, for example, comprise metal or plastic foil, such as a blister pack. The pack may be accompanied by instructions for administration. The pack may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription APIs or of an approved product insert. Devices including APIs as described herein may be placed in an appropriate packaging and/or labeled for treatment of an indicated condition, as is detailed herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

BIBLIOGRAPHY

Bhardwaj, R., et al. *Gut* 46(6):861-868 (2000).
Briel, J. W., et al. *Int. J. Colorectal. Dis.* 15(4): 253-254 (2000).
Carapeti, E. A., et al. *Gut* 44(5):727-730 (1999).
Carapeti, E. A., et al. *Dis. Colon Rectum* 43(10):1359-1362 (2000).
Cook, T. A., et al. *Aliment. Pharmacol. Ther.* 15: 887-898 (2001).
Gorfine, S. R. *Dis. Colon Rectum.* 38(5):453-456 (1995).
Griffin, N., et al. *Colorectal Dis.* 4(6):430-435 (2002).
Gui, D., et al. *Lancet* 344: 1127-1128 (1994).
Guillemot, F., et al. *Dis. Colon Rectum* 36(4):372-376 (1993).
Jensen, S. L., et al. *BMJ.* 292: 1167-1169 (1986).
Jost, W. H. *Dis. Colon Rectum* 40: 1029-1032 (1997).
Loder, P. B., et al. *Br. J. Surg.* 81 (9):1386-1389 (1994).
MacKay, D. *Altern. Med. Rev.* 6(2):126-140 (2001).
Schouten, W. R, et al. *Gut* 39(3):465-9 (1996).

What is claimed is:

1. A drug delivery device comprising:
    a shell sized for insertion in a rectum of a subject and which comprises within the shell a pharmaceutical composition,
    wherein the pharmaceutical composition comprises a pharmaceutically acceptable carrier and an active pharmaceutical ingredient,
    wherein the carrier is a solid at normal room temperature and has a melting point so as to melt due to a rectal temperature of the subject, and
    wherein the shell has an upper end and sides that are continuous, wherein the shell has a lower portion with an aperture, and wherein the upper end and sides are impermeable to the active pharmaceutical ingredient and impermeable to water; and
    a wick having a first portion extending from the inside of the shell and passing through the aperture of the shell, and a second portion positioned outside the shell, wherein:
    (i) the first portion is configured to contact the active pharmaceutical ingredient during delivery of the active pharmaceutical ingredient, and
    (ii) the second portion is positionable proximal to an anal sphincter upon insertion of the device into the rectum of the subject,
    wherein, when the device is inserted into the rectum of the subject, the carrier melts due to the rectal temperature of the subject, and the active pharmaceutical ingredient is released from the second portion of the wick proximal to the anal sphincter.

2. The device of claim 1 wherein an outer surface of the shell is provided with a lubricant layer.

3. The device of claim 2 wherein the lubricant layer comprises a local anesthetic.

4. The device of claim 1 wherein the shell is provided with a rounded tip.

5. The device of claim 1 wherein the shell is collapsible upon the release of the active pharmaceutical ingredient.

6. The device of claim 1 wherein the carrier further comprises at least one additional active pharmaceutical ingredient.

7. The device of claim 1 wherein the active pharmaceutical ingredient is selected from the group consisting of a herbal extract, bee pollen, a muscle relaxant, a local anesthetic, an antibiotic, an anti-inflammatory agent, a nitric oxide donor, botulinum toxin, a muscarinic agent, a sympathetic neuromodulator, a calcium channel antagonist, a phosphodiesterase inhibitor, a superoxide scavenger, a cyclic adenosine monophosphate-dependent protein kinase activator, an adenosine triphosphate-sensitive calcium channel activator and mixtures thereof.

8. The device of claim 7 wherein the calcium channel antagonist is nifedipine.

9. The device of claim 1 wherein the carrier is polyethylene glycol.

10. The device of claim 6 wherein the at least one additional active pharmaceutical ingredient is chosen from magnesium and salts thereof.

11. The device of claim 1 wherein the shell is configured to deform by pressure exerted thereon by the anal sphincter of the subject.

12. The device of claim 1 wherein the aperture is sized to enable release of the active pharmaceutical ingredient from the shell at a preselected rate.

13. A method of treating an anorectal disorder in a subject comprising:
providing the drug delivery device of claim 1; and
inserting the device into the rectum of the subject, such that the second portion of the wick is proximal to the anal sphincter of the subject, the carrier melts due to the rectal temperature of the subject, and the active pharmaceutical ingredient is released from the second portion of the wick proximal to the anal sphincter.

14. The method of claim 13 and further comprising releasing the active pharmaceutical ingredient to the anal sphincter.

15. The method of claim 14 wherein releasing comprises releasing the active pharmaceutical ingredient at a preselected rate.

16. The method of claim 13 further comprising deforming the shell.

\* \* \* \* \*